(12) United States Patent
Hete et al.

(10) Patent No.: US 11,925,765 B2
(45) Date of Patent: Mar. 12, 2024

(54) SYSTEMS AND METHODS FOR PROVIDING CONTROLLED SUPPLEMENTAL OXYGEN VIA ANY VENTILATOR

(71) Applicant: KONINKLIJKE PHILIPS N.V., Eindhoven (NL)

(72) Inventors: Bernard F Hete, Kittanning, PA (US); Peter R Doyle, Vista, CA (US); Kenneth E Cole, Jr., New Alexandria, PA (US); Robert William Murdoch, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 394 days.

(21) Appl. No.: 17/191,066

(22) Filed: Mar. 3, 2021

(65) Prior Publication Data
US 2021/0308410 A1     Oct. 7, 2021

Related U.S. Application Data

(60) Provisional application No. 63/040,573, filed on Jun. 18, 2020, provisional application No. 63/006,325, filed on Apr. 7, 2020.

(51) Int. Cl.
*A61M 16/12* (2006.01)
*A61M 16/00* (2006.01)
(Continued)

(52) U.S. Cl.
CPC ........ *A61M 16/122* (2014.02); *A61M 16/022* (2017.08); *A61M 16/0666* (2013.01);
(Continued)

(58) Field of Classification Search
CPC .............. A61M 16/122; A61M 16/022; A61M 16/0666; A61M 16/0833; A61M 16/12;
(Continued)

(56) References Cited

U.S. PATENT DOCUMENTS

| | | | |
|---|---|---|---|
| 4,072,148 A * | 2/1978 | Munson | A61M 16/12 137/601.01 |
| 4,602,653 A * | 7/1986 | Ruiz-Vela | A61M 16/12 128/204.22 |
| 5,237,987 A | 8/1993 | Anderson | |
| 5,701,883 A | 12/1997 | Hete | |

(Continued)

FOREIGN PATENT DOCUMENTS

| | | |
|---|---|---|
| CN | 102120054 A | 7/2011 |
| EP | 2985050 A1 | 2/2016 |
| FR | 3019992 A1 | 10/2015 |
| WO | 2020055933 A1 | 3/2020 |

OTHER PUBLICATIONS

International Search Report for PCT/EP2021/058830 filed Apr. 6, 2021.

*Primary Examiner* — Kendra D Carter
*Assistant Examiner* — Maap Ahmed Ellabib
(74) *Attorney, Agent, or Firm* — Daniel H. Brean

(57) ABSTRACT

A gas delivery apparatus configured for use with a mechanical ventilator having an atmospheric inlet for drawing in atmospheric gas includes a connecting device configured to connect to an oxygen supply and an air supply and to deliver mixed air and oxygen gas to the atmospheric inlet of the mechanical ventilator. The connecting device further includes a user control for adjusting a fraction of oxygen in the mixed air and oxygen gas. The connecting device comprises a reservoir configured to hold a volume of the mixed air and oxygen gas.

17 Claims, 5 Drawing Sheets

(51) Int. Cl.
*A61M 16/06* (2006.01)
*A61M 16/08* (2006.01)
*A61M 16/20* (2006.01)

(52) U.S. Cl.
CPC ........ *A61M 16/0833* (2014.02); *A61M 16/12* (2013.01); *A61M 16/201* (2014.02); *A61M 2016/003* (2013.01); *A61M 2202/0208* (2013.01)

(58) Field of Classification Search
CPC .............. A61M 16/201; A61M 16/125; A61M 16/0891; A61M 2016/003; A61M 2202/0208; A61M 39/10
See application file for complete search history.

(56) References Cited

U.S. PATENT DOCUMENTS

| | | | |
|---|---|---|---|
| 5,954,050 A * | 9/1999 | Christopher | A61M 16/085 128/204.26 |
| 6,412,483 B1 | 7/2002 | Bailey | |
| 7,849,854 B2 | 12/2010 | Cegielski | |
| 2003/0106554 A1* | 6/2003 | de Silva | A61M 16/12 128/204.22 |
| 2006/0191536 A1 | 8/2006 | Kroupa | |
| 2016/0045696 A1 | 2/2016 | Rao | |
| 2016/0095997 A1 | 4/2016 | Aguirre | |
| 2016/0158477 A1 | 6/2016 | Dhuper | |
| 2019/0083724 A1* | 3/2019 | Boulanger | A61M 16/0078 |
| 2019/0307981 A1 | 10/2019 | Ahmad | |

* cited by examiner

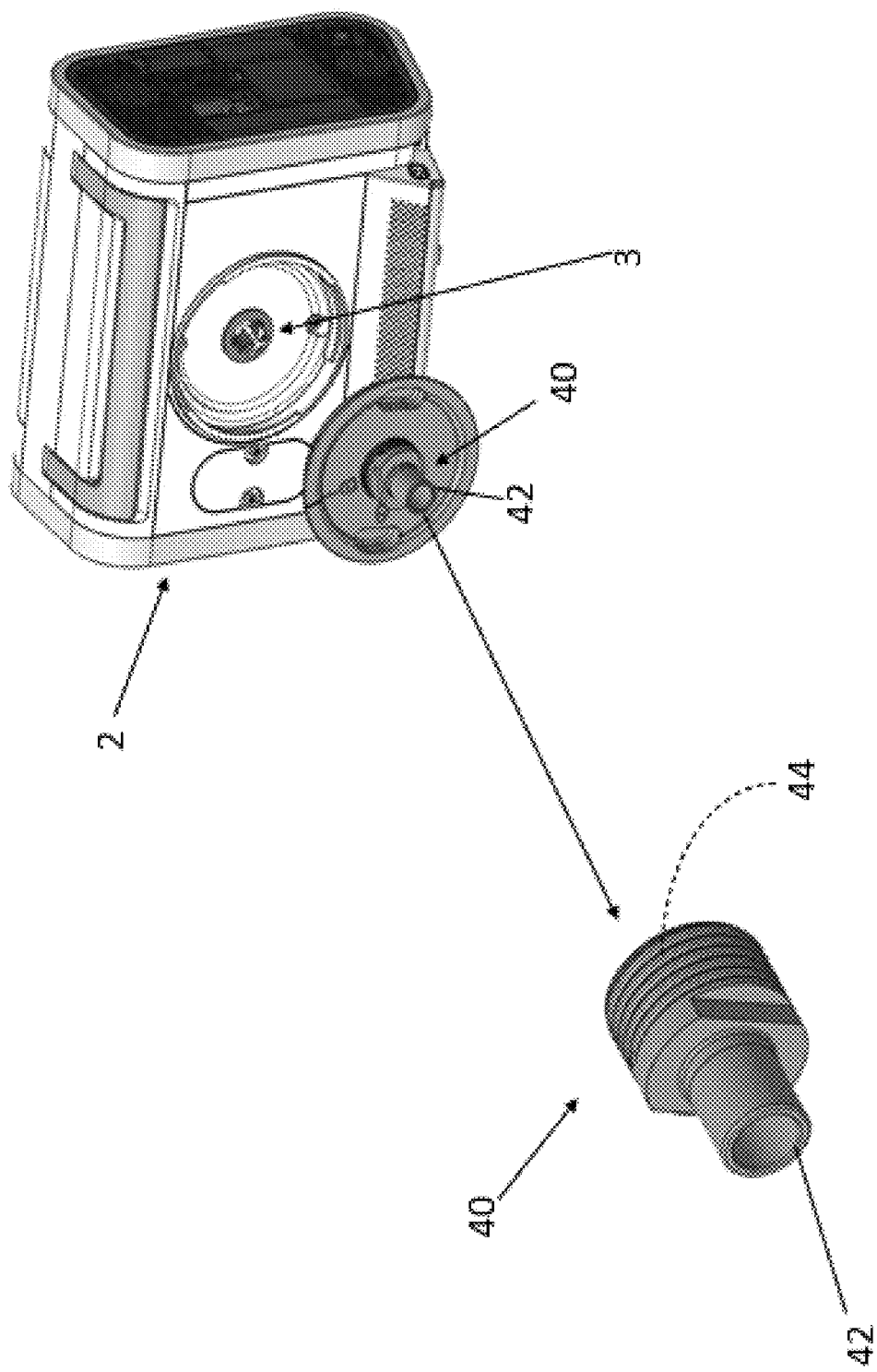

SYSTEMS AND METHODS FOR PROVIDING CONTROLLED SUPPLEMENTAL OXYGEN VIA ANY VENTILATOR

CROSS-REFERENCE TO RELATED APPLICATIONS

This patent application claims the priority benefit under 35 U.S.C. § 119(e) of U.S. Provisional Application Nos. 63/040,573 and 63/006,325, filed on Jun. 18, 2020 and Apr. 7, 2020, the contents of which are herein incorporated by reference.

The following relates generally to the ventilation therapy arts, in particular enabling any ventilator, including continuous positive airway pressure (CPAP) devices and bilevel positive airway pressure (BIPAP) devices, to provide supplemental oxygen therapy and related arts.

BACKGROUND

In view of infectious respiratory diseases, such as coronavirus (and specifically the COVID-19 pandemic), an effort is being made to greatly expand access to mechanical ventilation in medical facilities. In addition to increasing production of various ventilators, efforts abound to adapt many different types of ventilators to treat patients. A key requirement of such ventilators is the need to provide controlled supplemental oxygen between 50% and 100% fraction of inspired oxygen ($FiO_2$) or fractional oxygen. This is currently not doable with most ventilators that can be produced in very high quantities, such as sleep apnea treatment ventilators or CPAP machines.

For example, the Philips/Respironics Trilogy EVO ventilator can include an oxygen blending module (OBM) option, but world-wide supply chain limitations make it difficult to meet demand for such ventilators with OBMs, which is projected to be in the 20,000 to 36,000 per month range. As an alternative to ventilators such as the Trilogy EVO with OBM, there is a need to create a controlled $FiO_2$ between 21% and 100% for use as in ventilators that lack OBMs.

The following discloses certain improvements to overcome these problems and others.

SUMMARY

In one aspect, a gas delivery apparatus configured for use with a mechanical ventilator having an atmospheric inlet for drawing in atmospheric gas includes a connecting device configured to connect to an oxygen supply and an air supply and to deliver mixed air and oxygen gas to the atmospheric inlet of the mechanical ventilator. The connecting device further includes a user control for adjusting a fraction of oxygen in the mixed air and oxygen gas. The connecting device comprises a reservoir configured to hold a volume of the mixed air and oxygen gas.

In another aspect, a mechanical ventilation method includes: mixing, with a mixer, air from an air supply and oxygen gas from an oxygen supply to generate mixed air and oxygen gas; flowing the mixed air and oxygen gas to an atmospheric inlet of a mechanical ventilator; and adjusting a flow rate of the mixer to control a fraction of oxygen in the mixed air and oxygen gas.

One advantage resides in providing a mechanical ventilator with an adjustable $FiO_2$ setting.

Another advantage resides in providing a substantially constant, clinician controlled $FiO_2$.

Another advantage resides in providing an adapter for existing mechanical ventilators with OBMs.

Another advantage resides in providing a ventilator with a reservoir of mixed air and oxygen.

Another advantage resides in provider a ventilator with a reservoir of mixed air in fluid communication with an inlet of a ventilator.

Another advantage resides in providing a gas delivery apparatus that enables any pressure-support ventilator that does not have a designated oxygen mixing method or apparatus to deliver oxygenated air, preferably with a user control for adjusting the fraction of oxygen.

Another advantage resides in providing a gas delivery apparatus and corresponding method for retrofitting an existing ventilator to deliver oxygenated air.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

FIG. 2 shows an adapter connected to a ventilator of the system of FIGS. 1A, 1B, and 1C.

DETAILED DESCRIPTION

Figure 1A:
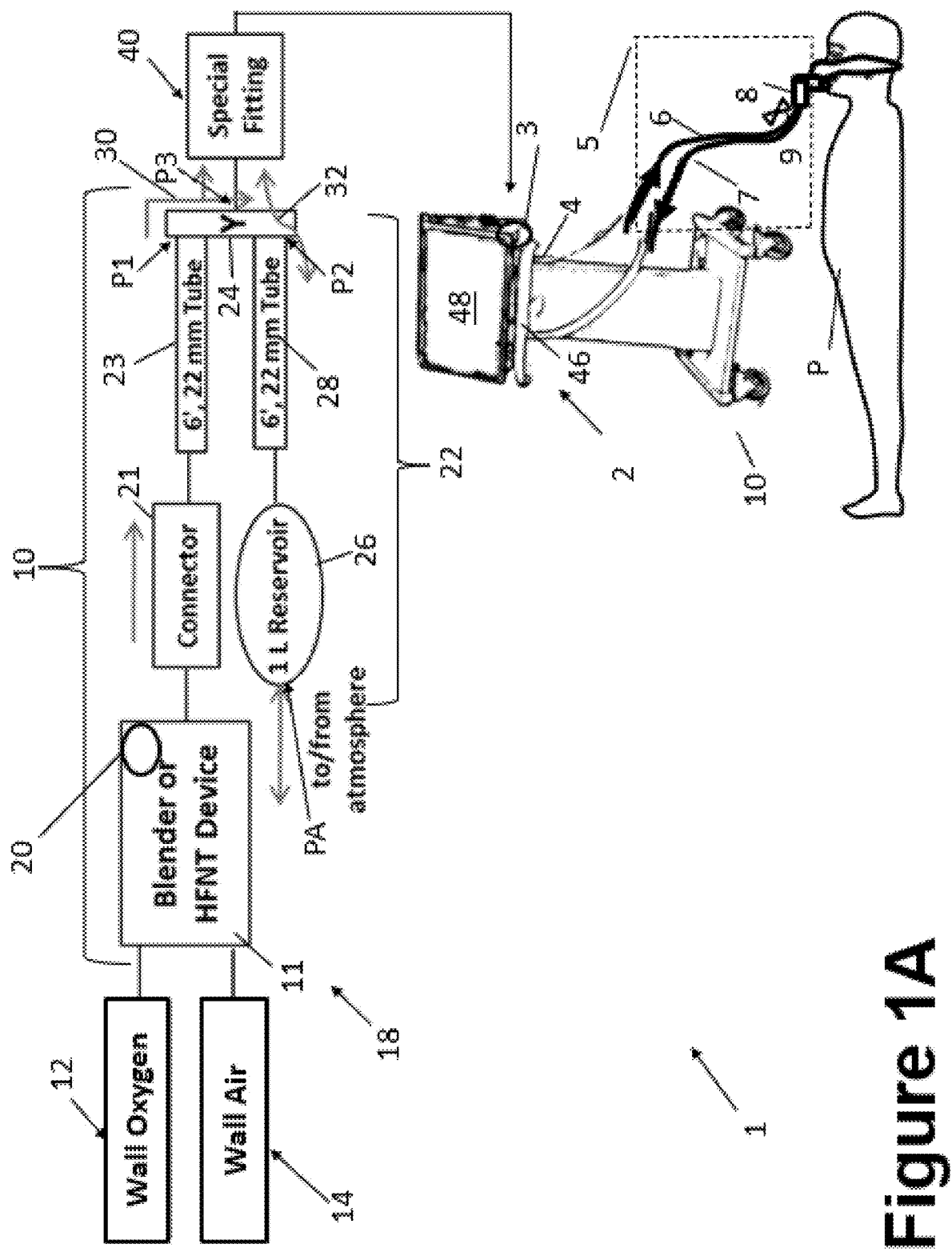
FIGS. 1A, 1B, and 1C diagrammatically show an illustrative apparatus for ventilator systems in accordance with the present disclosure.

As used herein, the singular form of "a", "an", and "the" include plural references unless the context clearly dictates otherwise. As used herein, statements that two or more parts or components are "coupled," "connected," or "engaged" shall mean that the parts are joined, operate, or coact together either directly or indirectly, i.e., through one or more intermediate parts or components, so long as a link occurs. Directional phrases used herein, such as, for example and without limitation, top, bottom, left, right, upper, lower, front, back, and derivatives thereof, relate to the orientation of the elements shown in the drawings and are not limiting upon the scope of the claimed invention unless expressly recited therein. The word "comprising" or "including" does not exclude the presence of elements or steps other than those described herein and/or listed in a claim. In a device comprised of several means, several of these means may be embodied by one and the same item of hardware.

Embodiments disclosed herein enable clinicians to provide controlled $FiO_2$ into any pressure support ventilator. The main elements of one non-limiting illustrative gas delivery apparatus or method include: (1) connection conduits/hoses for air and oxygen, such as from the hospital wall supply; (2) an oxygen blender/blending method of some sort; (3) a flow control method for either mixed gas or each gas separately; (4) an optional algorithm communicated to the user or clinician to allow them to set the correct flows; (5) a connector to a patient circuit; (6) a patient circuit such as a 22 mm, 6' standard patient circuit; (7) a 'Y' connection that connects 2 patient circuits, a connection to the ventilator and optionally a Positive End Expiratory Pressure (PEEP) valve; (8) a special connector that engages the pneumatic inlet to the ventilator that can connect to the 'Y' connection; (9) a serial section of two tubes, such as 22 mm, 6' tubes, connected to the 'Y' connection; and (10) optionally a PEEP valve as a safety measure to limit the pressure change at the ventilator inlet.

The approach described herein involves benefits of, inter alia, (1) leveraging existing capabilities and materials available in hospitals (i.e. wall $O_2$ and Air; $O_2$-Blenders); (2) minimizing the use of new parts, using readily available respiratory parts (i.e., 22 mm tubing, connectors, etc.); and being applicable to other platforms such as CPAP or BiPAP machines like the Philips/Respironics DreamStation (available from Koninklijke Philips NV, Eindhoven, the Netherlands).

Some non-limiting embodiments disclosed herein provide methods of making and using the systems described above. For example, the main elements of the disclosure described above may be connected with standard parts and fittings such that the user or clinician would be able to assemble the system according to a diagram and/or appropriate instructions.

These and other objects, features, and characteristics of the present disclosure, as well as the methods of operation and functions of the related elements of structure and the combination of parts and economies of manufacture, will become more apparent upon consideration of the following description and any appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

The disclosed gas delivery apparatuses and methods effectively replace the atmospheric gas drawn into the inlet of the vent with gas of the clinician specified $FiO_2$. By using this approach, the ventilator will operate normally since the goal is to provide the gas mixture at atmospheric pressure. In this fashion, any mode or function of the ventilator will continue to operate as normal.

The system includes a means of providing a controlled $FiO_2$ from hospital wall gas supplies, such as the use of rotameters, blenders, high flow nasal therapy (HFNT) devices, etc. that can supply up to 60 L/min. The system also includes a means to inform the clinician of the gas flow setting, which is equal to mean leak flow over a breath.

The system also includes a means of porting that gas to the inlet of the ventilator, such as a connection from the wall gas supply to a 6', 22 mm patient circuit attached to a "Y." The "Y" may be attached to a special fitting that connects to the specific ventilator (e.g., a Philips/Respironics Trilogy EVO ventilator, Trilogy ventilator, or DreamStation BiPAP—each having an appropriate interface fitting).

The system also includes a reservoir that is freely open to the atmosphere on one end that holds up to 1.5 L (although other capacities are contemplated) and is connected to the other branch of the "Y". This reservoir can be comprised of, for example, 12' of 22 mm tubing, or a single 6' of tubing, coupled to a 1 L bladder open on the opposite end from the connection to the tubing. The system may also include preferential use of a 22 mm circuit between the vent and the patient, which may include humidification, and which would accommodate all other normal aspects of a single or dual-limb limb patient interface.

In some embodiments, the system delivers high flows to the patient circuit due to the use of a fixed-orifice exhalation valve in a single-limb circuit, which leaks flow proportional to circuit pressure. Depending on ventilator settings, this typically requires flows that are a factor of, for example, 3-10 times patient minute volume (for example, a typical adult has a patient minute volume of 5-10 L/min).

A basic description of each part of an exemplary embodiment will now be provided.

Wall Gas—Supplies of air and oxygen of fifty psi each are provided at each bed in the hospital. They can be accessed with standard fittings. These pressures can have a wide tolerance is U.S. medical facilities, particularly in situ when high volumes of gas are being used during a pandemic. Also, supply pressures may vary widely at medical facilities around the world.

Gas $FiO_2$ Delivery—There are a number of methods for gas blending. One method uses a Traditional Gas Blender and Rotameter/Flowmeter—The only restriction on this approach is the availability of blenders in hospitals may be limited and the flow meter must be able to do up to 70 L/min, which is higher than what is normally used in such devices. Setting the $FiO_2$ requires merely dialing in the desired setpoint on the blender face. Another method uses a HFNT Device, which are high flow devices that can deliver constant flow rates at specified $FiO_2$ values. They can be connected as the source to the inlet of the supply tube. Another method uses a Dual-Rotameter. This approach requires separate rotameters on the air and oxygen supplies that then allows the gas to be blended downstream. Setting the $FiO_2$ by the user suitably employs an empirical or calculated table to allow setting of the two flows to allow the total to achieve a specified $FiO_2$ at a given bulk flow.

Connector—This is a fitting that connects the blending outlet to the 6', 22 mm patient circuit. Its form would be dependent on the method chosen for blending.

6', 22 mm Tube and "Y" Assembly—Blended gas would enter, via the Connector, a standard 6' circuit attached to a "Y". At this point, the gas should substantially be near atmospheric pressure, which is desired at the inlet to the vent. The "Y" would then connect to the Special Fitting. A second limb of the 6', 22 mm tubing would then be attached to the other leg of the "Y". This leg allows gas to accumulate upstream from the vent when vent flow is less than blender flow (during exhalation), allowing a reservoir from which to draw gas back in for use when the vent flow exceeds the blender flow (occurs during inspiration).

Reservoir—Extra volume at the end of the second tube. Its volume should be 1 L, allowing a total accumulation volume of 1.7 L (a 6', 22 mm tube has a volume of about 0.7 L), which is required to cover most ventilation cases. It is imperative that the reservoir be vented to atmosphere so as not to allow pressure to build up in front of the vent. It is also preferable that this volume be shaped in the form of a tube in order to limit the $FiO_2$ gas from mixing either with atmospheric air, or with the mixture that previously resided in this reservoir.

Special Fitting—This is a fitting that would allow the "Y" of the dual-limb circuit to be connected to the inlet of the ventilator with a seal so that no atmospheric air can leak into the vent. Such a fitting could be adapted for each ventilator that uses this blended oxygen approach. This technology could be applied to any ventilator or sleep therapy device for which a Special Fitting can be adapted.

Setting the Flow Rate—The system uses a model to predict the required flow rate based on an estimation of the ventilator minute volume. The ventilator minute volume is defined as $$\dot{V}_{ventilator} = V_{T_{ventilator}} \times \Psi$$

where $\dot{V}_{ventilator}$ is the minute volume of the ventilator (L/min), $V_{T_{ventilator}}$ is the volume delivered by the vent per breath (L/breath) and $\Psi$ is the patient breath rate (breath/min). The ventilator minute volume, also known as the average leak flow, is often calculated and displayed by the ventilator.

The blended gas flow rate could be equal to the ventilator minute volume times a factor like 1.2. The actual factor value is suitably derived empirically, but preliminary data indicate that this approach is effective. The system may also be configured to communicate this value to the clinician. The ventilator may calculate and display this value, which can be accomplished via a software change, or it could be provided in accompanying literature. Because the value may be estimated just from delivered pressure, however, it can also be calculated or tabulated for the clinician very easily.

Figure 1B:
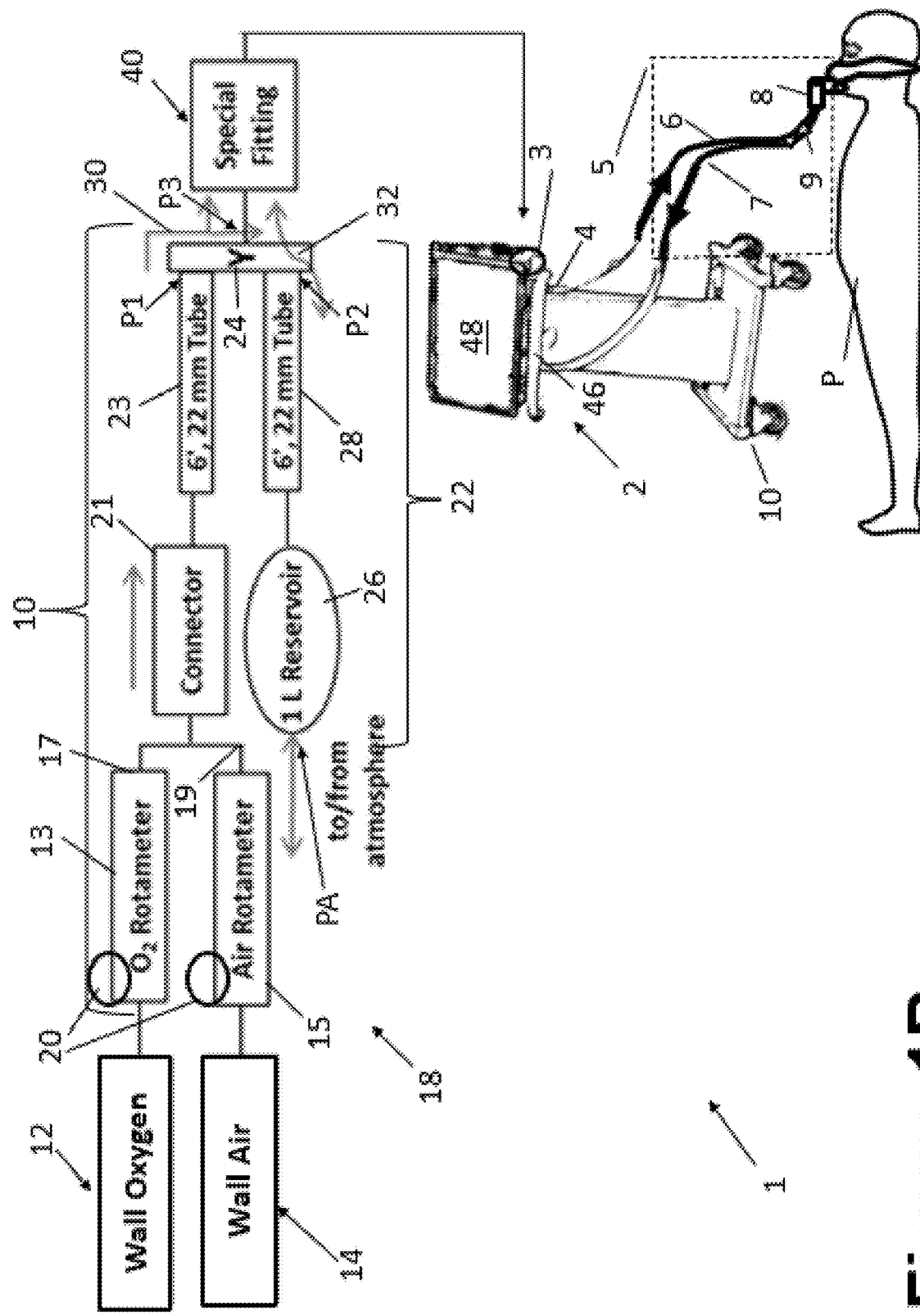
Figure 1C:
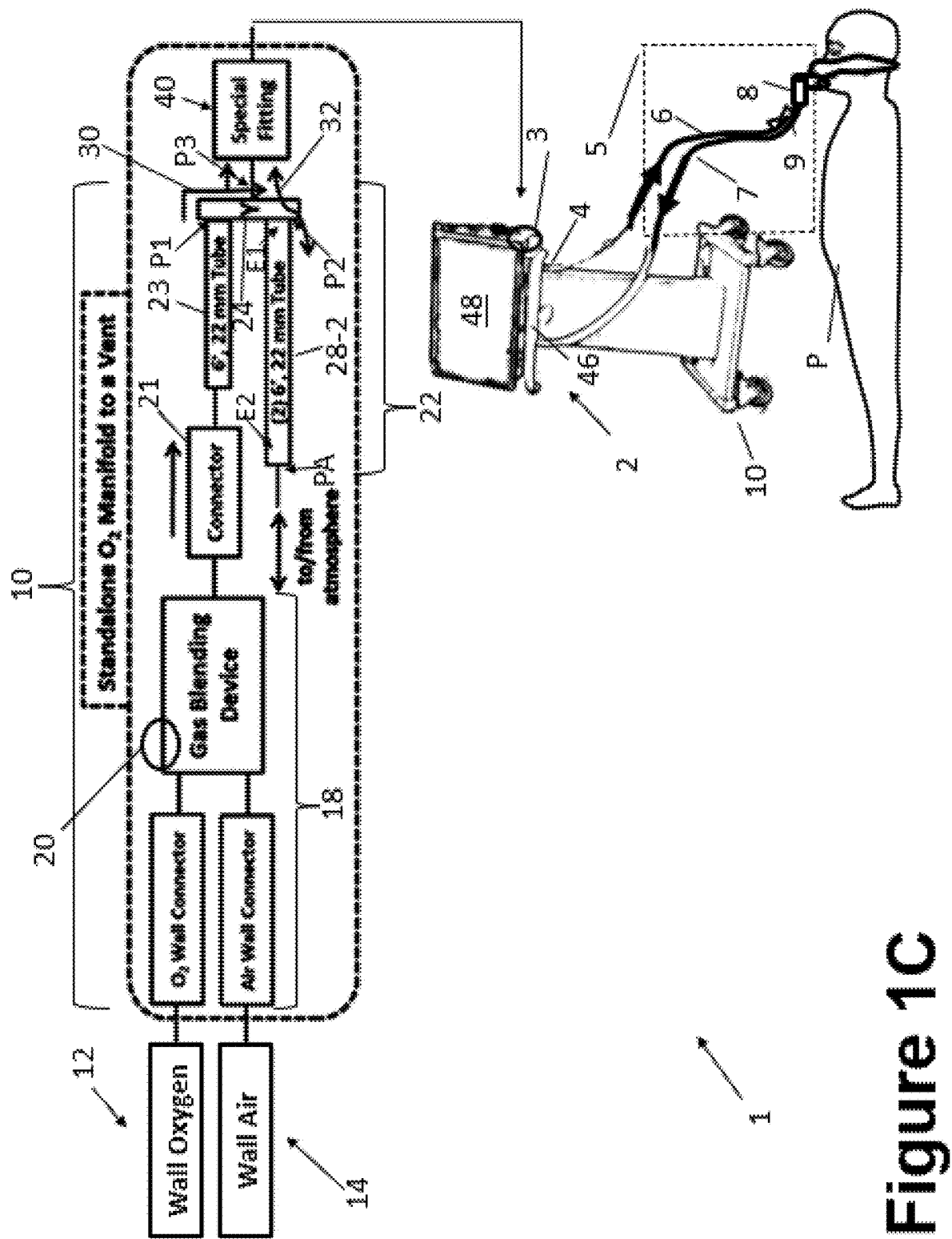

With reference to FIGS. 1A, 1B, and 1C, a mechanical ventilator system 1 for providing ventilation therapy to an associated patient P is shown. As shown in FIGS. 1A and 1B, the system 1 includes a mechanical ventilator 2, which can be a continuous positive airway pressure (CPAP) device, a bilevel positive airway pressure (BIPAP) device, or any other suitable mechanical ventilator (e.g., a Philips/Respironics Trilogy EVO ventilator, available from Koninklijke Philips NV). The mechanical ventilator 2 includes an atmospheric inlet 3 for drawing in atmospheric gas, and an outlet 4 connectable with a patient breathing circuit 5 to delivery mechanical ventilation to the patient P. The patient circuit 5 includes typical components for a mechanical ventilator, such as an inlet line 6, an optional outlet line 7 (this may be omitted if the ventilator employs a single-limb patient circuit), a patient port 8, an exhalation valve 9 (this may be omitted if the ventilator employs a dual-limb patient circuit), and one or more breathing sensors (not shown), such as a gas flow meter, a pressure sensor, end-tidal carbon dioxide (etCO$_2$) sensor, and/or so forth. The patient port 8 can be variously embodied. For non-invasive ventilation, the patient port 8 is suitably a mask strapped to the patient's face. For invasive ventilation, the patient port 8 may be an endotracheal tube, tracheostomy tube, or so forth. The disclosed approaches for delivering mixed air and oxygen gas to the atmospheric inlet 3 of the mechanical ventilator 2 may be generally employed in conjunction with any patient port design.

FIGS. 1A, 1B, and 1C also show a gas delivery apparatus 10, 40 configured to deliver mixed air and oxygen gas to the atmospheric inlet 3 of the mechanical ventilator 2. The atmospheric inlet 3 is also variously referred to herein as the inlet 3 of the mechanical ventilator 2 or as the pneumatic inlet 3 to the ventilator. The mechanical ventilator 2 is designed to draw atmospheric air in via the inlet 3 which is delivered to the outlet 4 to ventilate the patient. The inlet 3 may include threading or some other attachment for receiving a filter that removes particulates and optionally other contaminants from the drawn air. The mechanical ventilator 2 includes an electronic processor 46, and a display 48.

The gas delivery apparatus 10 connects with this inlet 3 via a special fitting 40 to instead supply mixed air and oxygen gas at (about) atmospheric pressure. As shown in FIGS. 1A, 1B, and 1C, the gas delivery apparatus 10 is connected with an oxygen supply 12 and an air supply 14, both of which are suitably standard wall oxygen 12 and wall air 14 supply outlets mounted on a wall of a room of a medical facility where the ventilation system 1 is deployed. Such wall oxygen and wall air (as well as wall vacuum) are ubiquitous in hospitals and other medical facilities. The wall oxygen 12 supplies oxygen at (nominally) 50 pounds per square inch (50 psi) according to common practice in the United States; however, it is common for the actual oxygen supply pressure to vary somewhat depending on extent of usage and other factors (e.g., the supply of oxygen gas may be 50 psi+ or −10 psi). Likewise, the wall air 14 supplies air at 50 psi; however, it is common for the actual air supply pressure to vary somewhat depending on extent of usage and other factors (e.g. the supply of air may be 50 psi+ or −10 psi). The nominal pressure may be different in various localities. For example, in Europe the oxygen supply is typically nominally around 60-70 psi.

In the gas delivery apparatus, the oxygen supply 12 and the air supply 14 are connected with a connecting device 10 that connects the oxygen and air supplies with the mechanical ventilator 2 (e.g., via the special fitting 40 of the gas delivery apparatus in the illustrative examples). The connecting device 10 is configured to deliver mixed air and oxygen gas to the atmospheric inlet 3 of the mechanical ventilator 2 (by way of the special fitting 40 in the illustrative examples). To do so, the connecting device 10 includes a mixer 18 configured to mix oxygen gas from the oxygen supply 12 and air from the air supply 14 to generate a mixture of mixed air and oxygen gas. As shown in FIG. 1A, the mixer 18 comprises a blender or a flow nasal therapy device (FNTD) 11. By contrast, FIG. 1B shows an embodiment in which the mixer 18 includes a first rotameter 13 connected to control a flow rate of oxygen from the oxygen supply 12, and a second rotameter 15 connected to control a flow rate of air from the air supply 14. An outlet 17 of the first rotameter 13 and an outlet 19 of the second rotameter 15 are connected together form the mixed air and oxygen gas. These are merely illustrative embodiments, and the mixer 18 may be otherwise embodied so as to combine oxygen from the wall oxygen 12 and air from the wall air 14 to produce the mixed air and oxygen gas.

The connecting device 10 further includes a user control 20 allowing a medical professional to adjust a fraction of oxygen in the mixed air and oxygen gas. As shown in FIG. 1A, the user control 20 comprises a user control (e.g., a knob, a button, a slider, and so forth) of the blender or FNTD 11. In FIG. 1B, the user control 20 suitably includes two flow control knobs—one for controlling the oxygen (O$_2$) rotameter 13 and the other for controlling the air rotameter 15. The mixer 18 is configured to mix oxygen from the oxygen supply 12 with air from the air supply 14 at a controlled total rate of a flow of mixed air of approximately 12-50 L/min. This rate can be adjusted with the user control 20.

The connecting device 10 further includes a flow path of the mixed air and oxygen gas from an outlet connector 21 of the mixer 18 to the atmospheric inlet 3 of the mechanical ventilator 2. In FIGS. 1A-1C, this flow path of the mixed air and oxygen gas to the atmospheric inlet 3 of the mechanical ventilator 2 includes a 6', 22 mm tube 23 connecting at one end with a mixer outlet connector 21 and at the other end with the special fitting 40. As will be explained, the flow path of the mixed air and oxygen gas to the atmospheric inlet 3 of the mechanical ventilator 2 further includes a branch connector 24, e.g. an illustrative "Y" connector 24, or a "T" connector, or so forth. The illustrative branch connector 24 has three ports: a port P1 connected with the 6', 22 mm tube 23 to receive the mixed air and oxygen gas from the mixer 18; a port P2 connected with a reservoir 22 to be described; and a port P3 connected with an inlet of the special fitting 40 and thus serving to flow the mixed air and oxygen into the atmospheric inlet 3 of the mechanical ventilator 2 via the fitting 40.

The connecting device 10 includes the reservoir 22 which is configured to hold a volume of the mixed air and oxygen gas. The reservoir 22 is connected with the flow path 23, 24 of the mixed air and oxygen gas to the atmospheric inlet 3 of the mechanical ventilator 2 by way of connection with the port P2 of the branch connector 24. The reservoir 22 is also open to atmosphere at a port PA. The illustrative reservoir 22 of FIGS. 1A and 1B includes a bladder 26 connected with the port P2 of the branch connector 24 by way of a 6', 22 mm tube 28. The volume of the mixed air and oxygen gas held in the reservoir 22 of FIGS. 1A and 1B is thus the sum of the volume of the bladder 26 and the volume contained by the tube 28.

In the embodiment of FIG. 1C, the illustrative reservoir 22 omits the bladder and instead includes two 6', 22 mm tubes 28-2 connected in series, with one end connected to port P2 of the branch connector 24 and the other end open to air. Hence, the volume corresponds to the volume of 12-feet of 22 mm diameter tubing. More generally, embodiments corresponding to FIG. 1C comprise a tube 28-2 having: a first end E1 connected with the flow path 23, 24 of the mixed air and oxygen gas to the atmospheric inlet 3 of the mechanical ventilator 2; and a second end E2 open to atmosphere. The volume is thus $\pi(d/2)^2 L$ where d is the diameter of the inner lumen of the tube and L is the total length of the tube. In embodiments in which the length L is large (e.g., 12-feet long in the embodiment of FIG. 1C), the tube 28-2 may be coiled up to reduce its size. An advantage of using a tube 28-2 as the reservoir 22 is that if the tube lumen diameter d is sufficiently small then gas inside the tube will be mixed primarily by diffusion, rather than by convection, which can increase the uniformity of the oxygen fraction in the mixed gas contained in the reservoir 22.

The port PA may be an opening to atmosphere of the bladder 26 (FIGS. 1A and 1B), or may be the open end E2 of the tube 28-2 (FIG. 1C). While the reservoir 22 is open to atmosphere via the port PA, it is to be understood that this does not preclude inclusion of a dust filter or the like at the port PA (or elsewhere, such as near the special fitting 40) which may introduce some flow resistance, so long as that flow resistance is not so large as to prevent the pressure of the mixed oxygen and air gas inside the reservoir 22 from reaching beyond a few cmH$_2$O above or below ambient atmospheric pressure. For example, the port PA may have a mesh filter, a foam filter, or the like to suppress ingress of dust or other debris into the reservoir 22. Furthermore, in the embodiment of FIG. 1C, if the tube 28-2 is coiled up, then this coiled-up tube may optionally be placed inside a mesh bag or the like (not shown) so long as the mesh of the bag does not substantially impede air flow into, or mixed gas flow out of, the port PA. An advantage of such a mesh bag is that it may reduce the potential for a nurse or other medical professional who notices the open end E2 of the tube from installing a cover plug under the mistaken assumption that the end E2 should not be open, or from trying to mistakenly try to connect the open tube to some other port.

Providing the reservoir 22 configured to hold a volume of the mixed air and oxygen gas has substantial benefits. It allows the flow rate of the supplied air and oxygen gas to be reduced, because at times when "extra" gas is needed, such as during inhalation, mixed air and oxygen gas can be drawn in from the reservoir 22; whereas, when "too much" gas is being supplied by the mixer 18 (such as during exhalation), the excess air and oxygen gas flow replenishes the reservoir 22. The benefit of minimizing wall gas usage is that, under COVID-19 pandemic conditions (or other pandemic conditions), oxygen usage is known to be compromised in some medical facilities because of high oxygen usage through the medical facility. Furthermore, by having the reservoir 22 connected with the flow path 23, 24 of the mixed air and oxygen gas to the atmospheric inlet 3 of the mechanical ventilator 2, and further having the reservoir is open to atmosphere, the pressure inside the reservoir is naturally maintained at about atmospheric pressure. Any excess flow of mixed air and oxygen gas to the reservoir is vented to atmosphere via the port PA. Any excess draw of mixed air and oxygen gas from the reservoir 22 can be accommodated by drawing air into the reservoir via the port PA. However, this latter situation may be slightly disadvantageous as it can dilute the oxygen concentration of the volume of the mixed air and oxygen contained in the reservoir 22. Nonetheless, such dilution will be negligibly small if the reservoir has sufficient capacity, as described later herein.

The operation is diagrammatically indicated in FIGS. 1A-1C by way of diagrammatically indicated flow arrows 30, 32. The mixer 18 supplies the mixed air and oxygen gas which flows into the special fitting 40, as indicated by the horizontal arrowhead of flow arrow 30. Any excess flow of mixed air and oxygen gas from the mixer 18 flows into the reservoir 22 as indicated by the downward arrowhead of flow arrow 30 and by the leftward arrowhead of flow arrow 32. Such excess typically occurs during exhalation. On the other hand, if the flow from the mixer 18 is insufficient to supply the patient (this is typically during inhalation), then mixed air and oxygen gas is supplied by the reservoir 22, as indicated by the rightward arrowhead of flow arrow 32 and the horizontal arrowhead of flow arrow 30.

The reservoir 22 is configured to hold a volume of the mixed air and oxygen gas that is greater than a volume of the flow path 23, 24 of the mixed air and oxygen gas to the atmospheric inlet 3 of the mechanical ventilator 2. For example, in some non-limiting embodiments suitable for use with the Philips/Respironics Trilogy EVO mechanical ventilator, the volume of the mixed air and oxygen gas held by the reservoir 22 is 0.5 L (or less), while the volume of the mixed air and oxygen gas in the flow path 23, 24 can be, for example, 0.7 L. By allowing the reservoir 22 to vent to the atmosphere via port PA and holding a volume of mixed air and oxygen gas that is greater than the volume in the flow path 23, 24, the reservoir 22 can control the flow of the mixed air and oxygen gas to the mechanical ventilator 2. As such, in some non-limiting embodiments, the gas delivery apparatus 10 is not configured to receive any control signal from the mechanical ventilator 2. This is because no such control signal is needed to control operation of the gas delivery apparatus 10, as the reservoir 22 open to air provides passive regulation of the flow to the atmospheric inlet 3.

The gas delivery apparatus 10 also includes the aforementioned special fitting 40 configured to connect the connecting device 10 (and more particularly port P3 of the branch connector 24) with the atmospheric inlet 3 of the mechanical ventilator 2. As previously mentioned, typically the mechanical ventilator 2 is designed to draw atmospheric air in via the atmospheric inlet 3. As such, there is usually no need to connect a gas supply to the atmospheric inlet 3. However, the atmospheric inlet 3 may include threading or other connection hardware for attaching a dust filter or the like, and this may be leveraged to simplify the construction of the special fitting 40.

With reference to FIG. 2, and with continuing reference to FIGS. 1A, 1B, and 1C, the fitting 40 includes an inlet 42 that connects with port P3 of the Y-connector 24, and an outlet 44 configured to make a sealed connection with the atmospheric inlet 3 of the mechanical ventilator 2. The outlet 44 of the fitting is configured to make sealed connection with the atmospheric inlet 3 of the mechanical ventilator 2.

The gas delivery apparatus 10 is, in some non-limiting embodiments, configured for use with a plurality of different mechanical ventilators 2 having different respective atmospheric inlets 3 for drawing in atmospheric gas. To do so, a ventilator retrofit package includes a plurality (or set) of specialized fittings corresponding to various different atmospheric inlets of different mechanical ventilators 2. Each specialized fitting 40 has the same inlet 42 but has its outlet 44 configured to make sealed connection with the atmospheric inlet 3 of the corresponding mechanical ventilator 2. This allows the same connecting device 10 to be used to deliver controlled oxygen to any make or model of mechanical ventilator for which a suitable specialized fitting is included in the set of specialized fittings of the retrofit package. In a medical crisis situation such as an outbreak of a highly contagious respiratory disease in which many patients may need to be ventilated with supplemental oxygen, this provides substantial flexibility to medical personnel in leveraging existing mechanical ventilators to deliver controlled oxygen, even with mechanical ventilators such as CPAP or BiPAP devices that are not conventionally capable of providing oxygen therapy.

As best shown in FIG. 2, an example of the fitting 40 for use with, for example, Philips/Respironics Trilogy EVO mechanical ventilator 2 is shown. As shown in FIG. 2, the fitting 40 that would allow the "Y" connector 30 of the dual-limb circuit (here "dual limb circuit" refers to the two limbs attached to ports P1 and P2 of the branch connector 24 and not to a dual-limbed patient circuit) to be connected to the inlet 3 of the mechanical ventilator 2 with a seal so that no atmospheric air can leak into the ventilator. Such a fitting 40 could be adapted for each ventilator 2 that uses this blended oxygen approach. For the Trilogy EVO adaptor fitting 40, an existing CBRN filter adaptor (e.g., a part labeled 1130506) may be used in conjunction with the fitting 40. In some examples, a length of tubing (not shown) can be added to connect the port P3 of the Y-connector 24 with the fitting 40. In other examples, the fitting 40 can comprise a flexible or sealable coupling capable of being universally or semi-universally connect with the mechanical ventilator 2 instead of being designed for a given vent (i.e., the atmospheric inlet 3).

The fitting 40 can be machined and/or molded to meet commercialization demands. The fitting 40 in this example provides a standard 22 mm ISO connection to interface with this proposed $O_2$ blending solution while interfacing to the mechanical ventilator 2 with a NATO standard thread. The fitting 40 may, for example, be machined aluminum, cleaned for 02 use and clear anodized. Alternatively, the fitting 40 may be injection-molded and produced from a myriad of different thermoplastics.

Figure 3:
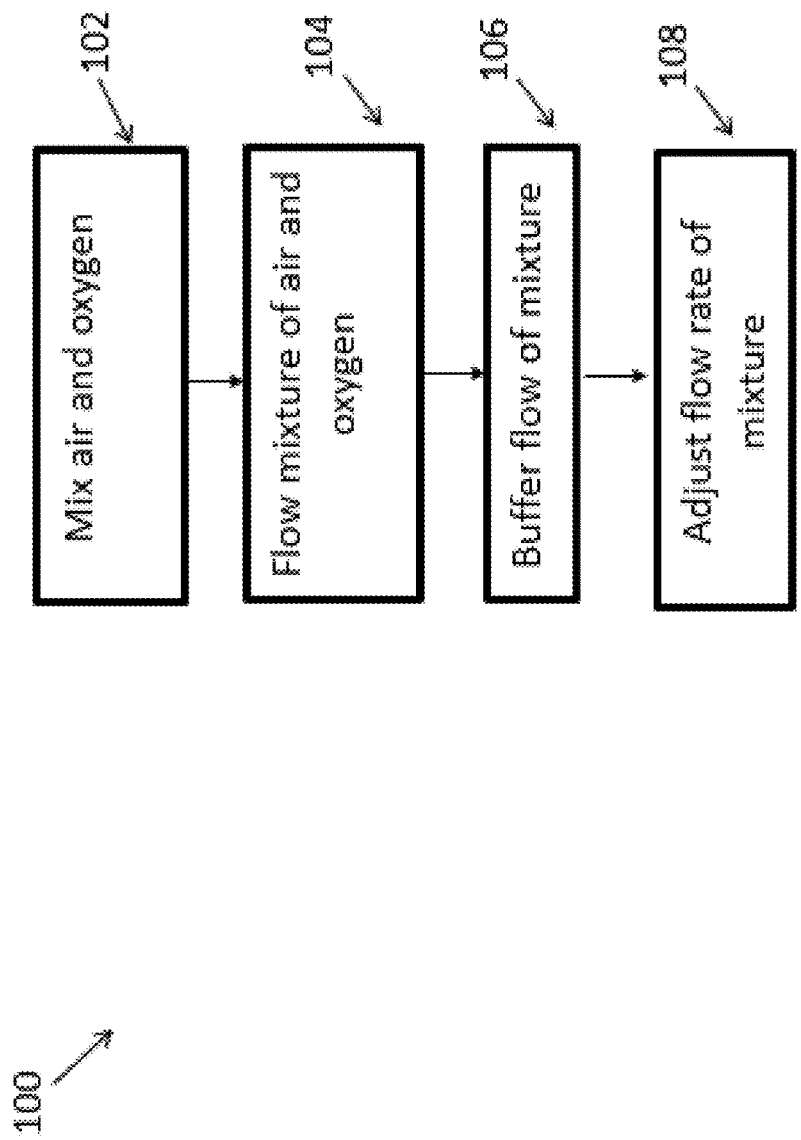
FIG. 3 shows an example flow chart of operations suitably performed by the systems of FIGS. 1A, 1B, and 1C.

With reference to FIG. 3, and with continuing references to FIGS. 1A, 1B, 1C, and 2, a mechanical ventilation method 100 performed by the gas delivery apparatus 10 is shown. At an operation 102, air from the air supply 14 and oxygen gas from the oxygen supply 12 are mixed with mixer 18 to generate a volume of mixed air and gas. At an operation 104, the mixed air and oxygen gas are flowed by the tube 23 from the mixer 18 to the atmospheric inlet 3 of the mechanical ventilator 2.

At an operation 106, the flow of the mixed air and oxygen gas is buffered using the reservoir 32. In one example, the buffering operation 106 can include venting the opening PA of the reservoir 22 to atmosphere. In another example, the buffering operation 106 includes providing the tube 28-8 with a first end E1 in fluid connection with the flowing mixed air and oxygen gas and a second end E2 that is open to atmosphere.

At an operation 108, a flow rate of the mixer 18 is adjusted to control a fraction of oxygen (e.g., $FiO_2$) in the mixed air and oxygen gas using the user control 20. For example, the flow rate of the mixer 18 can be adjusted to be set to an average leak of the mechanical ventilator 2 according to $\dot{V}_{ventilator} = V_{T_{ventilator}} \times \Psi$, in which $\dot{V}_{ventilator}$ is a minute rate of the mechanical ventilator 2, $V_{T_{ventilator}}$ is a volume delivered by the mechanical ventilator, and $\Psi$ is a patient breath rate. This calculation can be performed by the processor 46 of the mechanical ventilator 2, and can be output to the medical professional via the display 48 of the mechanical ventilator. However, this is merely an illustrative example. In another contemplated embodiment, if the mechanical ventilator 2 measures the fractional oxygen ($FiO_2$) and reports that on the display 48, then the clinician can merely adjust the user control 20 to set the $FiO_2$ to the desired value. If the ventilator does not report $FiO_2$ then a dedicated $FiO_2$ monitor (not shown) could be used to measure the $FiO_2$ value. Again, these are illustrative examples.

The disclosed gas delivery apparatus including the connecting device 10 and special fitting 40 can be deployed with substantially any type of mechanical ventilator. It may be used with either a single-limbed patient circuit or a dual-limbed patient circuit.

In another variant embodiment, rather than connecting the reservoir 22 to a branch connector 24, the specialized fitting could include an auxiliary port at which the reservoir 22 connects. This auxiliary port would be in addition to the inlet 42 and outlet 44 of the illustrative fitting 40, and would effectively turn the specialized fitting itself into a branched connector.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A gas delivery apparatus configured for use with a mechanical ventilator having an atmospheric inlet for drawing in atmospheric gas, the gas delivery apparatus comprising:
   a connecting device configured to connect to an oxygen supply and an air supply and to deliver mixed air and oxygen gas to the atmospheric inlet of the mechanical ventilator, the connecting device further including a user control for adjusting a fraction of oxygen in the mixed air and oxygen gas;
   wherein the connecting device comprises a reservoir configured to hold a volume of the mixed air and oxygen gas, wherein the reservoir is connected with a flow path of the mixed air and oxygen gas to the atmospheric inlet of the mechanical ventilator, and the reservoir is open to atmosphere, wherein the volume of the mixed air and oxygen gas held by the reservoir is greater than a volume of the flow path of the mixed air and oxygen gas to the atmospheric inlet of the mechanical ventilator.

2. The apparatus of claim 1, wherein the reservoir comprises a tube having:
a first end connected with the flow path of the mixed air and oxygen gas to the atmospheric inlet of the mechanical ventilator; and
a second end open to atmosphere.

3. The apparatus of claim 1, wherein the reservoir comprises a bladder connected with the flow path of the mixed air and oxygen gas to the atmospheric inlet of the mechanical ventilator; and further having:
an opening to atmosphere.

4. The apparatus of claim 1, wherein the volume of the mixed air and oxygen gas held by the reservoir is 0.5 L or less.

5. The apparatus of claim 1, wherein the reservoir is in fluid communication with atmosphere.

6. The apparatus of claim 1, wherein the connecting device further comprises:
a mixer configured to mix oxygen gas from the oxygen supply and air from the air supply to generate the mixed air and oxygen gas;
wherein the user control for adjusting the fraction of oxygen in the mixed air and oxygen gas comprises a user control of the mixer.

7. The apparatus of claim 6, wherein the mixer comprises one of:
a blender or a flow nasal therapy device; or
a first rotameter connected to control a flow rate of oxygen from the oxygen supply and a second rotameter connected to control a flow rate of air from the air supply, wherein an outlet of the first rotameter and an outlet of the second rotameter are connected together form the mixed air and oxygen gas.

8. The apparatus of claim 6, wherein the mixer is configured to mix oxygen from the oxygen supply with air from the air supply at a controlled total rate of a flow of mixed air of approximately 12-50 L/min.

9. The apparatus of claim 8, configured to not receive any control signal from the mechanical ventilator.

10. The apparatus of claim 8, further including:
a fitting having an inlet and further having an outlet configured to make sealed connection with the atmospheric inlet of the mechanical ventilator;
a flow path connected to transfer the mixed air and oxygen gas from the mixer to the inlet of the fitting;
wherein the reservoir is connected with the flow path or with the fitting.

11. The apparatus of claim 10, wherein:
the gas delivery apparatus is configured for use with a plurality of different mechanical ventilators having different respective atmospheric inlets for drawing in atmospheric gas; and
the fitting comprises a plurality of specialized fittings corresponding to the plurality of different mechanical ventilators, each specialized fitting having its outlet configured to make sealed connection with the atmospheric inlet of the corresponding mechanical ventilator.

12. A mechanical ventilator system, comprising:
a mechanical ventilator having:
an atmospheric inlet for drawing in atmospheric gas; and
an outlet connectable with a patient circuit to deliver mechanical ventilation to an associated patient; and
a gas delivery apparatus as set forth in claim 1 connected to deliver the mixed air and oxygen gas to the atmospheric inlet of the mechanical ventilator.

13. The mechanical ventilator system of claim 12, wherein the mechanical ventilator is a continuous positive airway pressure (CPAP) device or a bilevel positive airway pressure (BIPAP) device.

14. A mechanical ventilation method, comprising:
a gas delivery apparatus configured for use with a mechanical ventilator having an atmospheric inlet for drawing in atmospheric gas;
the gas delivery apparatus comprising: a connecting device configured to connect to an oxygen supply and an air supply;
wherein the connecting device comprises a mixer and a reservoir;
wherein the reservoir is configured to hold a volume of the mixed air and oxygen gas and is connected with a flow path of the mixed air and oxygen gas to the atmospheric inlet of the mechanical ventilator, and the reservoir is open to atmosphere;
wherein the method comprises: mixing, with the mixer, air from the air supply and oxygen gas from the oxygen supply to generate mixed air and oxygen gas;
flowing the mixed air and oxygen gas to the atmospheric inlet of the mechanical ventilator;
and adjusting a flow rate of the mixer to control a fraction of oxygen in the mixed air and oxygen gas;
wherein the volume of the mixed air and oxygen gas held by the reservoir is greater than a volume of the flow path of the mixed air and oxygen gas to the atmospheric inlet of the mechanical ventilator.

15. The mechanical ventilation method of claim 14, further comprising: buffering the flowing of the mixed air and oxygen gas to the atmospheric inlet of the mechanical ventilator using the reservoir.

16. The mechanical ventilation method of claim 15, wherein the buffering includes providing a tube having a first end in fluid connection with the flowing mixed air and oxygen gas and a second end that is open to atmosphere.

17. The mechanical ventilation method of claim 16, wherein the adjusting comprises:
adjusting a flow rate of the mixer to an average leak of the mechanical ventilator (2) according to $\dot{V}_{ventilator} = V_{T_{ventilator}} \times \Psi$, in which according to is a minute rate of the mechanical ventilator, $V_{ventilator}$ is a volume delivered by the mechanical ventilator, and $\Psi$ is a patient breath rate.

* * * * *